(12) United States Patent
Zhan et al.

(10) Patent No.: US 11,653,892 B2
(45) Date of Patent: May 23, 2023

(54) COUNTING RESPONSE AND BEAM HARDENING CALIBRATION METHOD FOR A FULL SIZE PHOTON-COUNTING CT SYSTEM

(71) Applicant: CANON MEDICAL SYSTEMS CORPORATION, Otawara (JP)

(72) Inventors: Xiaohui Zhan, Vernon Hills, IL (US); Xiaofeng Niu, Vernon Hills, IL (US); Ilmar Hein, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 220 days.

(21) Appl. No.: 17/156,089

(22) Filed: Jan. 22, 2021

(65) Prior Publication Data

US 2022/0233162 A1 Jul. 28, 2022

(51) Int. Cl.
*A61B 6/00* (2006.01)
*A61B 6/03* (2006.01)
(Continued)

(52) U.S. Cl.
CPC .............. *A61B 6/585* (2013.01); *A61B 6/032* (2013.01); *A61B 6/4035* (2013.01);
(Continued)

(58) Field of Classification Search
CPC ..... A61B 6/4447; A61B 6/583; A61B 6/4035; A61B 6/4241; A61B 6/5258; A61B 6/585; A61B 6/032; A61B 6/482; A61B 6/035; A61B 6/542; A61B 6/545; A61B 6/42; A61B 6/582; A61B 6/544; A61B 6/4441; A61B 6/504; A61B 6/481; A61B 6/405; A61B 6/4042; A61B 6/484; A61B 6/4291; A61B 6/5205; G01T 7/005; G01T 1/17; G01T 1/20184; G01T 1/36; G01T 1/171; G01T 1/24; G06T 7/10; G06T 11/005;
(Continued)

(56) References Cited

U.S. PATENT DOCUMENTS

2006/0109949 A1* 5/2006 Tkaczyk ................. A61B 6/542
378/4
2007/0189443 A1* 8/2007 Walter ..................... G06T 7/136
378/4

(Continued)

FOREIGN PATENT DOCUMENTS

EP          3667370 A1    6/2020
WO    2019/039033 A1    2/2019

*Primary Examiner* — Irakli Kiknadze
(74) *Attorney, Agent, or Firm* — Oblon, McClelland, Maier & Neustadt, L.L.P.

(57) ABSTRACT

A method and a system for providing calibration for a polychromatic photon counting detector forward counting model. Measurements with multiple materials and known path lengths are used to calibrate the photon counting detector counting response of the forward model. The flux independent weighted bin response function is estimated using the expectation maximization method, and then used to estimate the pileup correction terms at plural tube voltage settings for each detector pixel. The beam hardening corrections are then applied to the measured projection data sinogram, and the corrected sinogram is reconstructed to the counting image at the selected single energy.

18 Claims, 5 Drawing Sheets

(51) Int. Cl.
*G06T 7/10* (2017.01)
*G01T 7/00* (2006.01)
*G06T 11/00* (2006.01)

(52) U.S. Cl.
CPC .......... *A61B 6/4241* (2013.01); *A61B 6/4447* (2013.01); *A61B 6/583* (2013.01); *G01T 7/005* (2013.01); *G06T 7/10* (2017.01); *G06T 11/005* (2013.01); *G06T 2207/10081* (2013.01); *G06T 2207/30004* (2013.01); *G06T 2211/40* (2013.01)

(58) Field of Classification Search
CPC ....... G06T 2211/40; G06T 2207/30004; G06T 2207/10081; G06T 7/0012; G06T 2207/30168; G06T 11/006; G06T 7/136; G01N 23/046; G01N 2223/303; G01N 2223/5055; G01N 2223/419; G01N 2223/423; G01N 2223/501
USPC ............................................... 378/4, 19, 207
See application file for complete search history.

(56) References Cited

U.S. PATENT DOCUMENTS

| | | | |
|---|---|---|---|
| 2016/0095560 A1 | 4/2016 | Nakai | |
| 2016/0113617 A1* | 4/2016 | Herrmann | A61B 6/032 |
| | | | 378/207 |
| 2016/0203620 A1 | 7/2016 | Zou et al. | |
| 2016/0235382 A1* | 8/2016 | Besson | A61B 6/032 |
| 2016/0242726 A1* | 8/2016 | Koehler | A61B 6/5205 |
| 2021/0121143 A1* | 4/2021 | Iniewski | A61B 6/585 |

* cited by examiner

COUNTING RESPONSE AND BEAM HARDENING CALIBRATION METHOD FOR A FULL SIZE PHOTON-COUNTING CT SYSTEM

BACKGROUND

Technical Field

The disclosure relates to counting response and beam hardening calibration in a full size photon counting computed tomography system.

Description of the Related Art

Computed tomography (CT) systems and methods are typically used for medical imaging and diagnosis. CT systems generally create projection images through a subject's body at a series of projection angles. A radiation source, such as an X-ray tube, irradiates the body of a subject and projection images are generated at different angles. Images of the subject's body can be reconstructed from the projection images.

Conventionally, energy-integrating detectors (EIDs) and/or photon-counting detectors (PCDs) have been used to measure CT projection data. PCDs offer many advantages including their capacity for performing spectral CT, wherein the PCDs resolve the counts of incident X-rays into spectral components referred to as energy bins, such that collectively the energy bins span the energy spectrum of the X-ray beam. Unlike non-spectral CT, spectral CT generates information due to different materials exhibiting different X-ray attenuation as a function of the X-ray energy. These differences enable a decomposition of the spectrally resolved projection data into different material components, for example, the two material components of the material decomposition can be bone and water.

Even though PCDs have fast response times, at high X-ray flux rates indicative of clinical X-ray imaging, multiple X-ray detection events on a single detector may occur within the detector's time response, a phenomenon called pileup. Left uncorrected, pileup effect distorts the PCD energy response and can degrade reconstructed images from PCDs. When these effects are corrected, spectral CT has many advantages over conventional CT. Many clinical applications can benefit from spectral CT technology, including improved material differentiation since spectral CT extracts complete tissue characterization information from an imaged object.

One challenge for more effectively using semiconductor-based PCDs for spectral CT is performing the material decomposition of the projection data in a robust and efficient manner. For example, correction of pileup in the detection process can be imperfect, and these imperfections degrade the material components resulting from the material decomposition.

In a photon counting CT system, the semiconductor based detector using direct conversion is designed to resolve the energy of the individual incoming photons and generate measurements of multiple energy bin counts for each integration period. Compared to the conventional scintillator based EID, the PCD measurement takes equal weight for each registered photon in a few different energy bins. It allows the generation of counting images with better signal-to-noise ratio as well as spectral images with multiple basis materials.

However, due to the detection physics in such semiconductor materials (e.g. CdTe/CZT), the detector energy response is largely deviated from ideal response by charge sharing, k-escape, and scattering effects in the energy deposition and charge induction process, as well as electronic noise in the associated front-end electronics. With the finite signal induction time, at high count-rate conditions, pulse pile-up also distorts the energy response. Due to sensor material non-uniformity and complexity of the integrated detection system, it is very difficult to do accurate modeling of such detector response for a photon-counting detector just based on physics theories or Monte Carlo simulations.

A counting image measurement uses all the registered photons in the detector above certain energy threshold. The accurate modeling of the detector response is required to resolve the attenuated line integral. Calibration methods have been proposed to solve similar problems in literature. The general idea is to use multiple transmission measurements of various known path lengths to modify the forward model such that it agrees with the calibration measurements, see Sidky et al., Journal of Applied Physics 97(12), 124701 (2005); Duan et al., Medical Physics 38(2), February, 2011; and Dickmann et al., Proc. SPIE 10573, Medical Imaging 2018: Physics of Medical Imaging, 1057311 (Mar. 9, 2018). A calibration method is developed to generate spectral image using multiple energy bin measurement in material decomposition. For counting image measurement, the model parameterization could be different, and likely be simplified. The beam hardening effect, described below, needs to be calculated and corrected based on the calibrated counting response.

Most CT reconstruction algorithms assume that the x-ray source is monochromatic. In reality, the x-ray source is polychromatic and the attenuation of x-rays through tissue is frequency (i.e., energy) dependent. Higher energy photons are attenuated less than lower energy photons, thus the x-rays reaching the detector are "harder" than those that left the source.

If not accounted for, artifacts because of the above effect, hereinafter called beam hardening artifacts, will appear in the reconstructed images. The primary contributors to beam hardening are soft tissues with densities close to water, as well as bone or iodine contrast in cardiac scans.

Artifacts may include cupping (for example, with soft tissue beam hardening) as well as dark streaks and bands which can affect clinical diagnosis. Bone beam hardening artifacts may include dark streaks or bands between high density bone structures, such as bones in the scull. A dark band present in heart muscle due to beam hardening in a cardiac scan may be interpreted as ischemia, for example.

Theoretically, beam hardening correction is not complicated. However, with the advanced CT configurations present in current scanners (for example bowtie filters for dose reduction, wide-angle cone beam geometry for fast volume image acquisition; etc.) beam hardening correction for clinical CT becomes more challenging.

A particularly challenging case is cardiac imaging where a high-density CT contrast agent (typically iodinated and contrast agent) is injected into the patient. In this case, there are three primary beam hardening sources: soft tissue, bone, and iodine. Most current beam hardening methods can only correct for two materials, not three.

In addition, with the development of novel contrasts targeting specific diseases in molecular CT imaging, it is possible to inject more than one contrast for clinical diagnoses, which requires a multi-material beam hardening correction method.

Numerous methods exist to counteract the effects of beam hardening. Hardware filters, such as bowtie filters, along with linearizing correction procedures are commonly used to reduce beam hardening effects.

Herein, a PCD detector counting response model and a calibration method, including a workflow for corresponding beam hardening correction, is described.

SUMMARY

The embodiments presented herein relate to a two-step calibration method for the polychromatic PCD forward counting model. First, estimation of the flux independent weighted counting response function $S_w(E)$ using the expectation maximization (EM) method is performed, followed by the estimation of the pileup correction term $P(E,N_{tot})$ based on the estimated $S_w(E)$. Once $S_w(E)$ is estimated from the calibration at each tube voltage (kVp) setting for each detector pixel, it is saved as a software calibration table on the system. Then it is used as an input to estimate the pileup correction terms $P(E,N_{tot})$ at higher flux scans. Both tables are then used for the calculation of the beam hardening correction to generate the counting image. The beam hardening calibration may use water only correction by estimating the water equivalent path lengths directly from the counting sinogram, or use an iterative method by estimating 2 basis material path lengths from the reconstructed image for a more accurate beam hardening calculation.

BRIEF DESCRIPTION OF THE DRAWINGS

The application will be better understood in light of the description which is given in a non-limiting manner, accompanied by the attached drawings in which.

DETAILED DESCRIPTION OF THE PREFERRED EMBODIMENTS

Reference throughout this specification to "one embodiment" or "an embodiment" means that a particular feature, structure, material, or characteristic described in connection with the embodiment is included in at least one embodiment of the application, but do not denote that they are present in every embodiment.

Thus, the appearances of the phrases "in one embodiment" or "in an embodiment" in various places throughout this specification are not necessarily referring to the same embodiment of the application. Furthermore, the particular features, structures, materials, or characteristics may be combined in any suitable manner in one or more embodiments.

Figure 1:
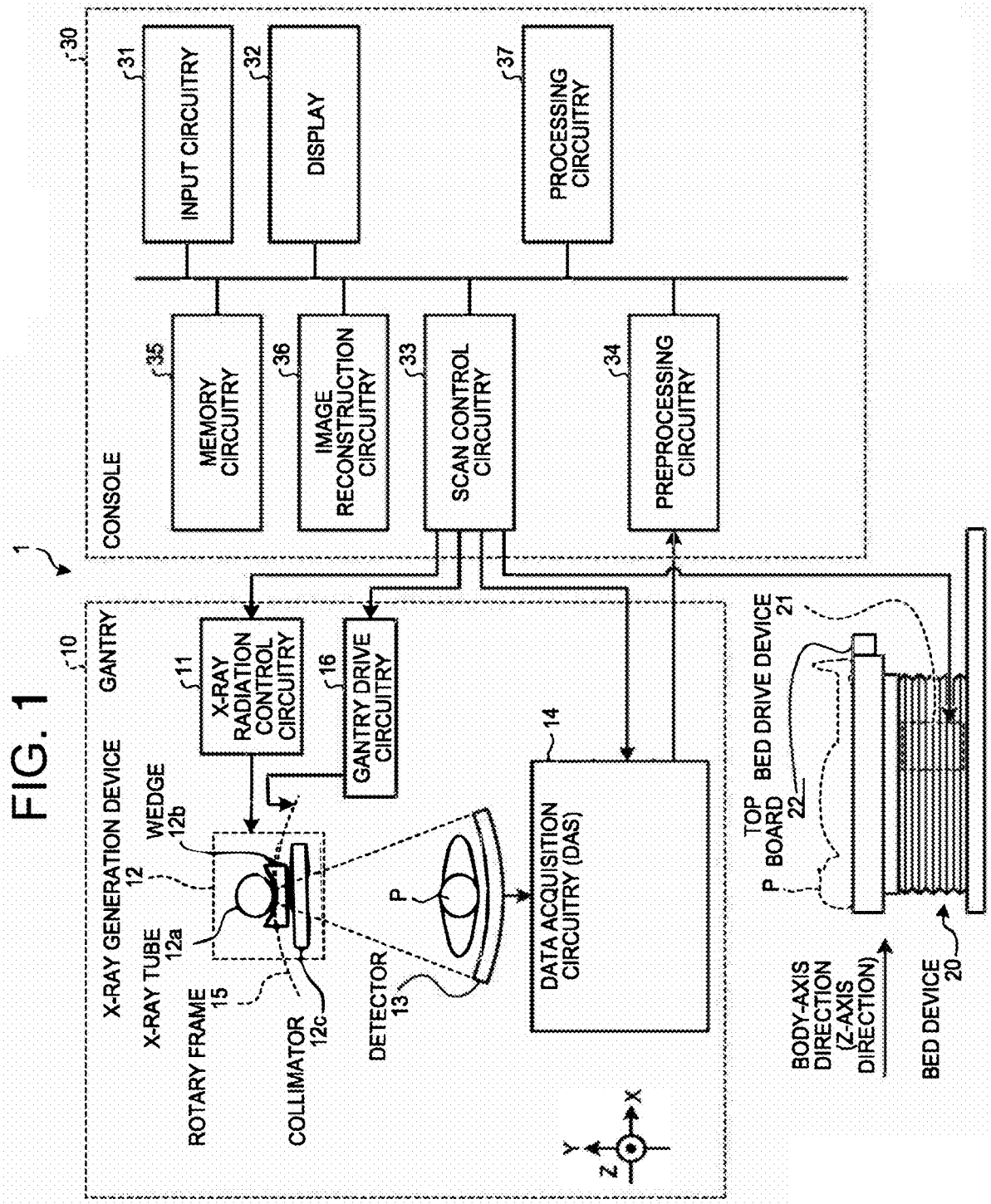
FIG. 1 shows an example of the configuration of a photon-counting type X-ray CT apparatus.

FIG. 1 is a diagram that illustrates an example of the configuration of a photon-counting type X-ray CT apparatus 1. As illustrated in FIG. 1, the photon-counting type X-ray CT apparatus 1 includes a gantry 10, a bed device 20, and a console 30.

The gantry 10 is a device that emits X-rays to a subject P (patient), detects the X-rays that are transmitted through the subject P, and outputs them to the console 30, and it includes X-ray radiation control circuitry 11, an X-ray generation device 12, a detector 13, data acquisition circuitry (DAS: Data Acquisition System) 14, a rotary frame 15, and gantry drive circuitry 16.

The rotary frame 15 is an annular frame that supports the X-ray generation device 12 and the detector 13 such that they are opposed to each other with the subject P interposed therebetween and that is rotated at high speed in a circular orbit around the subject P by the gantry drive circuitry 16.

The X-ray radiation control circuitry 11 is a device that serves as a high-voltage generation unit and supplies a high voltage to an X-ray tube 12a, and the X-ray tube 12a generates X-rays by using the high voltage that is supplied from the X-ray radiation control circuitry 11. Under the control of scan control circuitry 33, the X-ray radiation control circuitry 11 adjusts the tube voltage or the tube current that is supplied to the X-ray tube 12a, thereby adjusting the amount of X-rays that are emitted to the subject P.

Furthermore, the X-ray radiation control circuitry 11 switches a wedge 12b. Furthermore, the X-ray radiation control circuitry 11 adjusts the numerical aperture of a collimator 12c, thereby adjusting the radiation range (the fan angle or the cone angle) of X-rays. Moreover, there may be a case where multiple types of wedges are manually switched by an operator.

The X-ray generation device 12 is a device that generates X-rays and emits the generated X-rays to the subject P, and it includes the X-ray tube 12a, the wedge 12b, and the collimator 12c.

The X-ray tube 12a is a vacuum tube that emits X-ray beams to the subject P by using the high voltage that is supplied by the X-ray radiation control circuitry 11, and it emits X-ray beams to the subject P in accordance with the rotation of the rotary frame 15. The X-ray tube 12a generates X-ray beams that spread with the fan angle and the cone angle. For example, under the control of the X-ray radiation control circuitry 11, the X-ray tube 12a is capable of continuously emitting X-rays all around the subject P for a full reconstruction or continuously emitting X-rays for a half reconstruction within an emission range (180°+the fan angle) that enables a half reconstruction. Furthermore, under the control of the X-ray radiation control circuitry 11, the X-ray tube 12a is capable of intermittently emitting X-rays (pulse X-rays) at a previously set position (tube position). Furthermore, the X-ray radiation control circuitry 11 is capable of changing the intensity of X-rays, emitted from the X-ray tube 12a. For example, the X-ray radiation control circuitry 11 increases the intensity of X-rays, emitted from the X-ray tube 12a, at a specific tube position, and it decreases the intensity of X-rays, emitted from the X-ray tube 12a, in the area other than the specific tube position.

The wedge 12b is an X-ray filter that adjusts the amount of X-rays with regard to the X-rays that are emitted from the X-ray tube 12a. Specifically, the wedge 12b is a filter that transmits and attenuates X-rays, emitted from the X-ray tube 12a, such that X-rays, emitted from the X-ray tube 12a to the subject P, has a predetermined distribution. For example, the wedge 12b is a filter that is obtained by processing aluminum so as to have a predetermined target angle or a predetermined thickness. Furthermore, the wedge is also called a wedge filter or a bow-tie filter.

The collimator 12c is a slit that narrows the irradiation range of X-rays, of which the amount of X-rays has been adjusted by the wedge 12b, under the control of the X-ray radiation control circuitry 11.

The gantry drive circuitry 16 drives and rotates the rotary frame 15 so that the X-ray generation device 12 and the detector 13 are rotated in a circular orbit around the subject P.

Each time an X-ray photon enters, the detector 13 outputs the signal with which the energy value of the X-ray photon may be measured. The X-ray photon is, for example, an X-ray photon that is emitted from the X-ray tube 12a and is transmitted through the subject P. The detector 13 includes multiple detection elements that output an electric signal (analog signal) of 1 pulse each time an X-ray photon enters. The photon-counting type X-ray CT apparatus 1 counts the number of electric signals (pulses) so as to count the number of X-ray photons that enter each of the detection elements. Furthermore, the photon-counting type X-ray CT apparatus 1 performs arithmetic processing on the signal so as to measure the energy value of the X-ray photon that causes output of the signal.

The above-described detection element includes, for example, a scintillator and an optical sensor, such as a photomultiplier tube. In such a case, the detector 13, illustrated in FIG. 1, is an indirect-conversion type detector that converts the incident X-ray photon into scintillator light by using the scintillator and converts the scintillator light into an electric signal by using the optical sensor, such as a photomultiplier tube. Furthermore, there may be a case where the above-described detection element is a semiconductor device of, for example, cadmium telluride (CdTe), cadmium zinc telluride (CdZnTe), or the like. In such a case, the detector 13, illustrated in FIG. 1, is a direct-conversion type detector that directly converts the incident X-ray photon into an electric signal.

For example, the detector 13, illustrated in FIG. 1, is a plane detector in which detection elements are arranged in N columns in the channel direction (the direction of the X axis in FIG. 1) and in M columns in the direction of the rotational center axis of the rotary frame 15 (the direction of the Z axis in FIG. 1) where the gantry 10 is not tilted. When a photon enters, the detection element outputs an electric signal of one pulse. The photon-counting type X-ray CT apparatus 1 discriminates among individual pulses that are output from a detection element 131, thereby counting the number of X-ray photons that enter the detection element 131. Furthermore, the photon-counting type X-ray CT apparatus 1 performs arithmetic processing based on the intensity of a pulse, thereby measuring the energy value of the counted X-ray photon.

The data acquisition circuitry 14 is a data acquisition system (DAS), and it acquires the detection data on X-rays that are detected by the detector 13. For example, the data acquisition circuitry 14 generates the count data that is obtained by counting the photons (X-ray photons), which come from the X-ray that is transmitted through the subject, for each energy band, and it transmits the generated count data to the console 30 that is described later. For example, if X-rays are continuously emitted from the X-ray tube 12a while the rotary frame 15 is rotated, the data acquisition circuitry 14 acquires the group of count data for the entire periphery (360 degrees). The data acquisition circuitry 14 also can acquire data for each view. Furthermore, the data acquisition circuitry 14 transmits each acquired count data in relation to the tube position to the console 30 that is described later. The tube position is the information that indicates the projection direction of the count data.

The bed device 20 is a device on which the subject P is placed and, as illustrated in FIG. 1, it includes a bed drive device 21 and a top board 22. The bed drive device 21 moves the top board 22 in the direction of the Z axis to move the subject P into the rotary frame 15. The top board 22 is a board on which the subject P is placed. Furthermore, in the present embodiment, an explanation is given of a case where the relative position between the gantry 10 and the top board 22 is changed by controlling the top board 22; however, this is not a limitation on the embodiment. For example, if the gantry 10 is self-propelling, the relative position between the gantry 10 and the top board 22 may be changed by controlling driving of the gantry 10.

Furthermore, for example, the gantry 10 conducts helical scan to scan the subject P in a helical fashion by rotating the rotary frame 15 while the top board 22 is moved. Alternatively, the gantry 10 conducts conventional scan to scan the subject P in a circular orbit by rotating the rotary frame 15 with the position of the subject P fixed after the top board 22 is moved. Alternatively, the gantry 10 implements a step-and-shoot method to conduct conventional scan at multiple scan areas by moving the position of the top board 22 at a constant interval.

The console 30 is a device that receives an operation of the photon-counting type X-ray CT apparatus 1 from an operator and that reconstructs X-ray CT image data by using the projection data that is acquired by the gantry 10. As illustrated in FIG. 1, the console 30 includes input circuitry 31, a display 32, the scan control circuitry 33, preprocessing circuitry 34, memory circuitry 35, image reconstruction circuitry 36, and processing circuitry 37.

The input circuitry 31 includes a mouse, keyboard, trackball, switch, button, joystick, or the like, which is used by an operator of the photon-counting type X-ray CT apparatus 1 to input various commands or various settings, and it transfers the information on the command or setting, received from the operator, to the processing circuitry 37. For example, the input circuitry 31 receives, from an operator, a capturing condition for X-ray CT image data, a reconstruction condition for reconstructing X-ray CT image data, an image processing condition for X-ray CT image data, or the like.

The display 32 is a monitor that is viewed by an operator and, under the control of the processing circuitry 37, it displays the image data, generated from X-ray CT image data, to the operator or displays a graphical user interface (GUI) for receiving various commands, various settings, or the like, from the operator via the input circuitry 31.

The scan control circuitry 33 controls operations of the X-ray radiation control circuitry 11, the gantry drive circuitry 16, the data acquisition circuitry 14, and the bed drive device 21 under the control of the processing circuitry 37, thereby controlling data acquisition processing by the gantry 10. For example, scan control circuitry 33 sends sequence control commands to data acquisition circuitry 14 to control exposure operations, as discussed in more detail below.

The preprocessing circuitry 34 performs correction processing, such as logarithmic conversion processing, offset correction, sensitivity correction, or beam hardening correction, on the count data that is generated by the data acquisition circuitry 14, thereby generating corrected projection data.

The memory circuitry 35 stores the projection data that is generated by the preprocessing circuitry 34. Furthermore, the memory circuitry 35 stores the image data, or the like, which is generated by the image reconstruction circuitry 36 that is described later. Moreover, the memory circuitry 35 appropriately stores processing results of the processing circuitry 37 that is described later.

The image reconstruction circuitry 36 reconstructs X-ray CT image data by using the projection data that is stored in the memory circuitry 35. Here, the reconstruction method includes various methods, and it may be, for example, back projection processing. Furthermore, the back projection processing may include, for example, back projection processing by using a filtered back projection (FBP) method. Alternatively, the image reconstruction circuitry 36 may also use a successive approximation technique to reconstruct X-ray CT image data. Furthermore, the image reconstruction circuitry 36 conducts various types of image processing on X-ray CT image data, thereby generating image data. Then, the image reconstruction circuitry 36 stores, in the memory circuitry 35, the reconstructed X-ray CT image data or the image data that is generated during various types of image processing.

The processing circuitry 37 controls operations of the gantry 10, the bed device 20, and the console 30 so as to perform the overall control on the photon-counting type X-ray CT apparatus 1. Specifically, the processing circuitry 37 controls the scan control circuitry 33 so as to control CT scan that is conducted by the gantry 10. Furthermore, the processing circuitry 37 controls the image reconstruction circuitry 36 so as to control image reconstruction processing or image generation processing by the console 30. Furthermore, the processing circuitry 37 performs control such that various types of image data, stored in the memory circuitry 35, are displayed on the display 32.

Heretofore, the overall configuration of the photon-counting type X-ray CT apparatus 1 according to the first embodiment is explained. Here, each processing function, performed by each of the above-described circuitry, is stored in the memory circuitry 35 in the form of the program that is executable by the computer. Furthermore, each circuitry reads and executes each program from the memory circuitry 35, thereby performing the above-described various functions.

In one example, programs corresponding to the operations of the data acquisition circuitry 14 are stored in the memory circuitry 35 in the form of a program that is executable by a computer. Processor 37 executes the programs for data acquisition circuitry 14 and sends instructions to and controls data acquisition circuitry 14 to acquire data as well as controls the transfer data from data acquisition circuitry 14. In a second example, data acquisition circuitry 14 includes a processor that reads and executes each program from the memory circuitry 35 to implement the function that corresponds to each program.

Furthermore, the word "processor", used in the above explanations, means for example a central processing unit (CPU), a graphics processing unit (GPU), or a circuit, such as an application specific integrated circuit (ASIC), or a programmable logic device (e.g., a simple programmable logic device: SPLD, a complex programmable logic device: CPLD, or a field programmable gate array: FPGA). The processor reads and executes the program, stored in the memory circuitry, to perform the function. Furthermore, a configuration may be such that, instead of storing a program in the memory circuitry, a program is directly installed in a circuit of the processor. In this case, the processor reads and executes the program, installed in the circuit, to perform the function. Furthermore, with regard to the processors according to the present embodiment, instead of the case where each processor is configured as a single circuit, multiple independent circuits may be combined to be configured as a single processor to implement the function.

Figure 2:
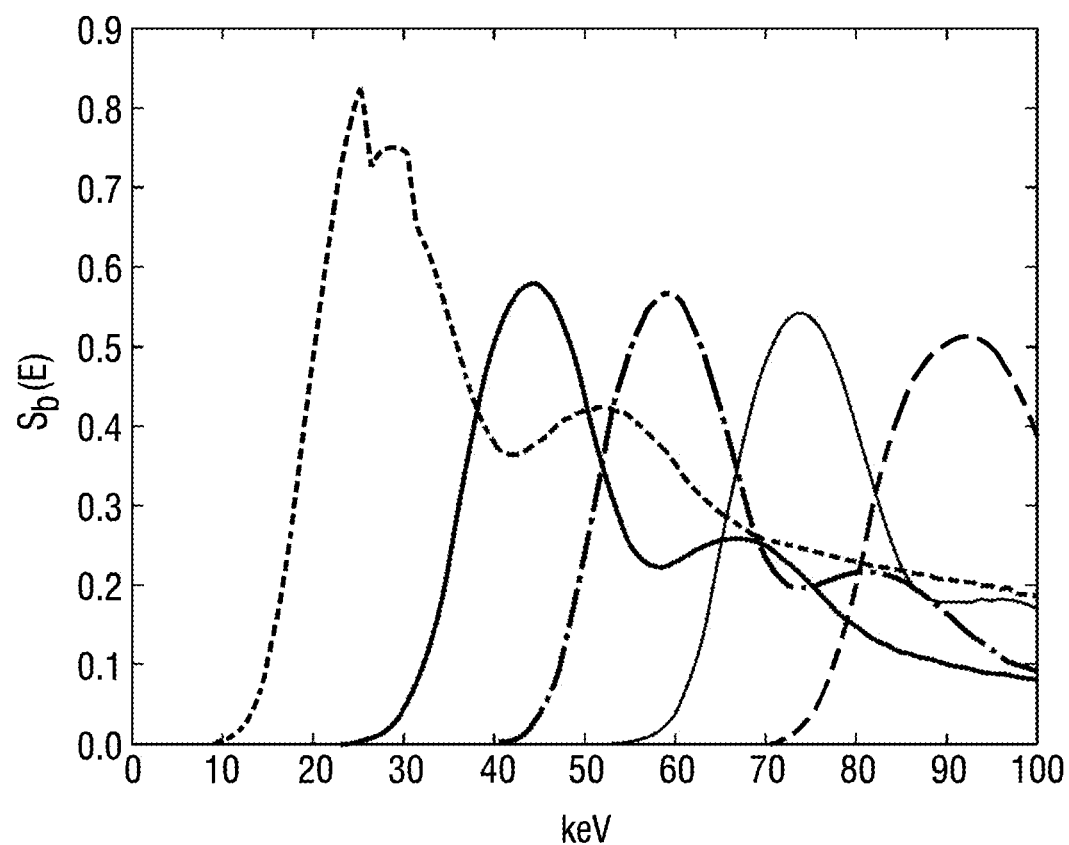
FIG. 2 shows an example of a PCD bin response function $S_b(E)$ for a photon counting detector. Each curve stands for an example function for each energy bin.

In a transmission measurement using a photon counting energy-resolving detector (PCD), the forward model can be formulated as below:

$$N_b(l_{1,...,M}) = N_0 \times \int dE \; w(E) S_b(E) \exp(-\Sigma \mu_m \; l_m), \quad (1)$$

where $S_b(E)$ denotes the bin response function defined as $S_b(E) = \int_{E_{bL}}^{E_{bH}} R(E,E') dE'$ where $R(E,E)$ is the detector response function, and $E_{bL}$ and $E_{bH}$ are the low and high energy threshold of each counting bin. FIG. 2 shows an example model of a typical (E) function for a PCD, where a long tail above the energy window is induced by charge sharing, k-escape and scattering effect. The low energy tail is mostly due to the finite energy resolution from the associated electronic noise. $N_0$ is the total flux from an air scan, $\mu_m$ and $l_m$ are the $m^{th}$ basis material linear attenuation coefficient and path length, respectively. $w(E)$ is the normalized incident X-ray spectrum. In practice, both $w(E)$ and $S_b(E)$ are not exactly known, and they can be combined as one term, $S_{wb}(E) = w(E) S_b(E)$, called thereafter the weighted bin response function.

For a high flux scan condition (e.g. a few percent of pulse pileup), pulse pileup introduces additional spectral distortion in the measurement. One way to correct for the pileup effect is to introduce additional correction and this type of additional calibration is based on an accurate estimation of the flux independent weighted bin response $S_{wb}(E)$. The forward model can be expressed as $$N_b(l_{1,...,M}) = N_0 \int dE S_{wb}(E) * P_b(E, N_b, N_{tot}) \exp(-\Sigma \mu_m \; l_m) \quad (2)$$

$P_b$ can be parameterized as a function of the energy, bin counts $N_b$ and the total count $N_{tot}$. Here, instead of using only two materials, as in prior arts (e.g., see Dickmann), the method uses 2-5 different materials such as polypropylene, water, aluminium, titanium/copper, and k-edge materials to calibrate the weighted bin response function $S_{wb}(E)$ at low flux. With more selective materials used in the calibration, the number of total path lengths is reduced to achieve equivalent or better results.

For a counting measurement, the total count $N_{tot}$ can be formulated as:

$$N_{tot} = N_0 \int dE \; S_w(E) * P(E, N_{tot}) \exp\left(-\int \mu(E, \vec{r}) \; dl\right) \quad (3)$$

where $S_w(E)$ is the flux independent weighted counting response function

If assuming only the total count $N_{tot}$ is available in the measurement, P is now a function of only E and $N_{tot}$, to account for both the counting and spectral related correction. For an ideal monochromatic measurement at energy $E_0$, the measurement is formulated as:

$$N_{tot} = N_0 \exp\left(-\int \mu(E_0, \vec{r}) \, dl\right) \quad (4)$$

The difference between Eqs. (3) and (4) constitutes the beam hardening correction for the polychromatic measurement. How to calibrate the counting detector response and calculate the beam hardening correction is addressed by the present disclosure.

Here, a two-step calibration method for the polychromatic PCD forward counting model is presented. It comprises two parts:

Step 1: estimation of the flux independent weighted counting response function $S_w(E)$ using the state of the art expectation maximization (EM) method;

Step 2: estimation of the pileup correction term $P(E,N_{tot})$ which can be a function of energy (E) and the measured total count $N_{tot}$. Once $S_w(E)$ is estimated from the calibration at each tube voltage (kVp) setting for each detector pixel, it is saved as a software calibration table on the system. It will be used as an input to estimate the pileup correction terms $P(E,N_{tot})$ at higher flux scans. Both tables will be used for the calculation of the beam hardening correction to generate the counting image.

For most materials, the attenuation coefficient can be decomposed into two basis materials, such as water and bone, or water and iodine. The forward counting model can be formulated as:

$$N_{tot}(l_{1,2}) = N_0 \int dE \, S_w(E) * P(E, N_{tot}) \exp(-\mu_1 l_1 - \mu_2 l_2) \quad (5)$$

where $\mu_1$ and $\mu_2$ are the linear attenuation coefficients for the chosen basis materials, e.g. water and bone, or water and iodine and $l_1$ and $l_2$ are the corresponding line integrals of the basis materials.

Flat slabs with selected basis materials and thicknesses will be placed in the scan field of view to cover the entire detector. The basic measurements will be done by stationary scans where the X-ray tube is parked at multiple fixed locations.

With an appropriate tube spectrum modelling to capture the characteristic peaks in the incident spectrum, and a physics based model to simulate the photon-counting detector spectral response, an initial estimate of $S_w(E)$ can be produced. By using EM method, see Sidky, $S_w(E)$ can be reliably estimated for this ill-conditioned problem based on a few transmission measurements.

A design variation for the pileup correction term P is to also use the measured bin counts $N_b$ in the parameterization, and $P(E,N_{tot},N_b)$ is calibrated using the same method as the above. The number of energy bins can be set from 2-6.

To calculate the beam hardening correction, with the calibrated detector response $S_w$ and P, one can just estimate the water equivalent path length sinogram based on the projection measurement, as water is a good approximation for most scanning object of human body.

For a more precise beam hardening correction, one can estimate the path lengths sinogram of the selected basis materials, e.g. water and bone, or water and iodine, using an iterative beam hardening correction workflow: the initial sinogram from the object scan is first generated without beam hardening correction, and an initial image is generated. The image is then segmented into basis material images. Then, a forward projection is applied to calculate the estimated basis material path lengths for each detector and each view. With the estimated path lengths, the beam hardening correction is calculated and applied on the original sinogram. The corrected sinogram will be reconstructed for the next iteration image, and go through another round of basis material path length estimation and correction if needed.

Figure 3:
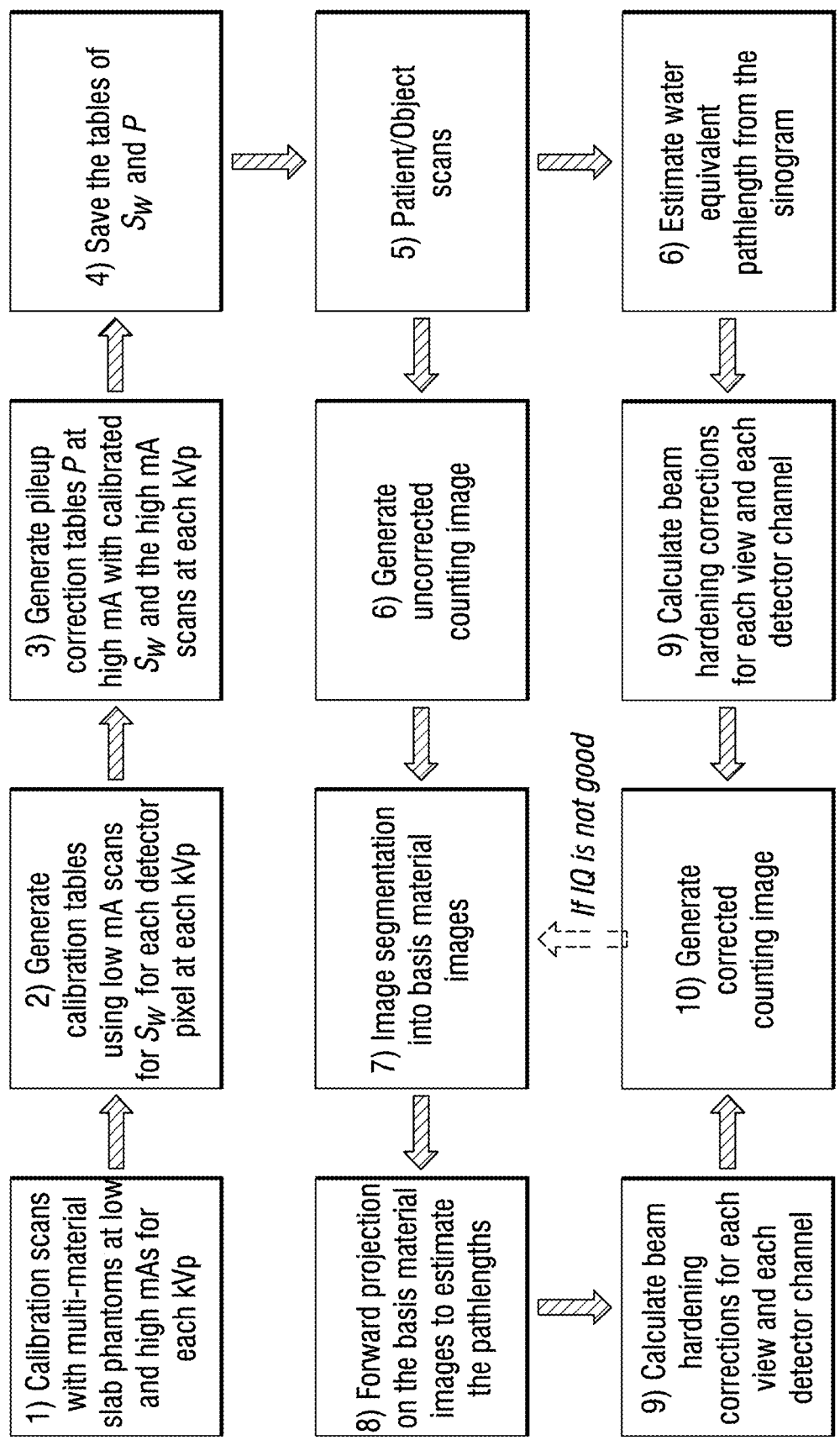
FIG. 3 shows a counting response and beam hardening calibration processing workflow.

The high level workflow is illustrated in FIG. 3. Steps 1) to 3) represent the counting response calibration workflow, and steps 4) to 10) represent the BHC workflow for two different BHC methods (Method 1 uses the water only correction by estimating the water equivalent path lengths directly from the counting sinogram. Method 2 uses an iterative method by estimating 2 basis material path lengths from the reconstructed image for a more accurate beam hardening calculation. This can be used in cases when Method 1 is not sufficient, e.g. head scans). The image quality is assessed with predefined standards, and if it is passed, the current corrected sinogram is saved and then used for the following patient/object scans data processing. Otherwise, the procedure goes through steps 7) to 9) in FIG. 3. Here, commonly examined standards are: image CT number accuracy, uniformity, spatial resolution, noise and artifacts. To check the quality of this calibration, these metrics should all be checked, especially the accuracy and artifacts like ring or bands in the image, which indicate the calibration is not good enough.

Detector Response Model

For the PCD counting response at low flux, $S_w$ is calibrated with low flux transmission measurements with different materials and pathlengths. This captures the count rate independent response of the counting measurement. Different from the individual bin counts required to perform material decomposition and generate spectral images, the calibration for $S_w$ only requires a total count measurement for which the photon is registered when it passes an energy threshold. Typically, one can set the threshold between 20 to 40 keV.

First, a series of low flux scans on various material slabs are collected at each tube kVp setting, which is the peak potential applied on the X-ray tube. Typical CT systems support a few kVp settings from 70 to 140 kVp which generate different energy spectrums from the X-ray tube for different scan protocol. For a CT scan, both mA and kVp need to be pre-selected before the tube is turned on. Then, the low flux weighted bin response function $S_w$ is estimated and with the estimated $S_w$, the high flux slab scans are used to estimate the additional parameters in the pileup correction term P. Finally, the estimation calibration tables of $S_w$ and P for each detector pixel are saved.

In order to satisfy the low flux condition through the calibration measurement to minimize the pileup effect in the flow diagram, step 1, one can select to use $n\tau < x$, where $x \sim 0.005$-$0.01$ and n is the pixel count rate with the lowest tube flux setting, and $\tau$ is the effective dead time of the PCD Application Specific Integrated Circuit (ASIC). By satisfying this condition, one can calculate the shortest path length of each selected calibration material, and the rest of path lengths can either be selected by equal spacing in path length or in resulting measurement count rate.

For the PCD counting response at high flux, a parameterization based on the photon energy E and the measured total counts $N_{tot}$ is used. The implementation of the front-end electronics (ASIC) can be approximated as a nonparalyzable model. Given an effective counting deadtime $\tau$, the measured count can be formulated as $$N_{tot} = \frac{N_{in}}{1 + N_{in}\tau} \quad (6)$$

Where $N_{in}$ is the incident total count on the detector surface. With an ideal detector counting response, $N_{in}$ can be expressed as:

$$N_{in} = N_0 \int dE \, \exp(-\mu_1(E)l_1 - \mu_2(E)l_2) \quad (7)$$

To employ this approximation with enough flexibility to account for certain deviation from the ideal nonparalyzable model due to complication in the real detection process and practical ASIC implementation, $P(E, N_{tot})$ is modelled as the following form:

$$P(E, N_{tot}) = \frac{1 + \Sigma a_n E^n + \Sigma b_n N_{tot}^n + \Sigma c_{nm} E^n N_{tot}^m}{1 + N_{in}\tau} \quad (8)$$

$$N_{in} = \frac{N_{tot}}{1 - N_{tot}\tau} \quad (9)$$

The polynomial terms based on $N_{tot}$ and E are introduced to account for variation from the nonparalyzable model, and are determined based on the high flux transmission measurements.

One parameterization variation is to include $N_b$ in P to better capture the spectral dependent response, so that:

$$P(E, N_{tot}, N_b) = \frac{1 + \Sigma a_n E^n + \Sigma b_n N_{tot}^n + \Sigma c_{nm} E^n N_{tot}^m + \Sigma d_n N_b}{1 + N_{in}\tau} \quad (10)$$

Estimation of Dead Time $\tau$

For the counting of dead time $\tau$ of each detector pixel, one can assume a universal value based on the ASIC design for every pixel. But it is possible that the counting performance is varied from pixel to pixel due to the actual design implementation. One can first estimate the effective dead time $\tau_i$ for each pixel i based on the measurements.

A set of air scans from low to high flux (mA) can first be collected, with each bowtie configuration. $\tau_i$ for each pixel can be estimated based on the counting curve measurement using the ideal nonparalyzable model, then used for the estimation of the pileup response term $P(E, N_{tot})$ or $P(E, N_{tot}, N_b)$.

The counting curve can also be measured with a certain material path length, e.g. 5-15 cm of water, and capture certain spectrum related counting response in P.

When estimating $\tau$ using those measurements, any numerical method can be used to find the solution by minimizing the weighted error square of the slab measurement 1 to j, $$\Sigma_j \left( \frac{(N_{tot} - N_{mod})^2}{\sigma_{tot}^2} \right)_j.$$

Figure 4:
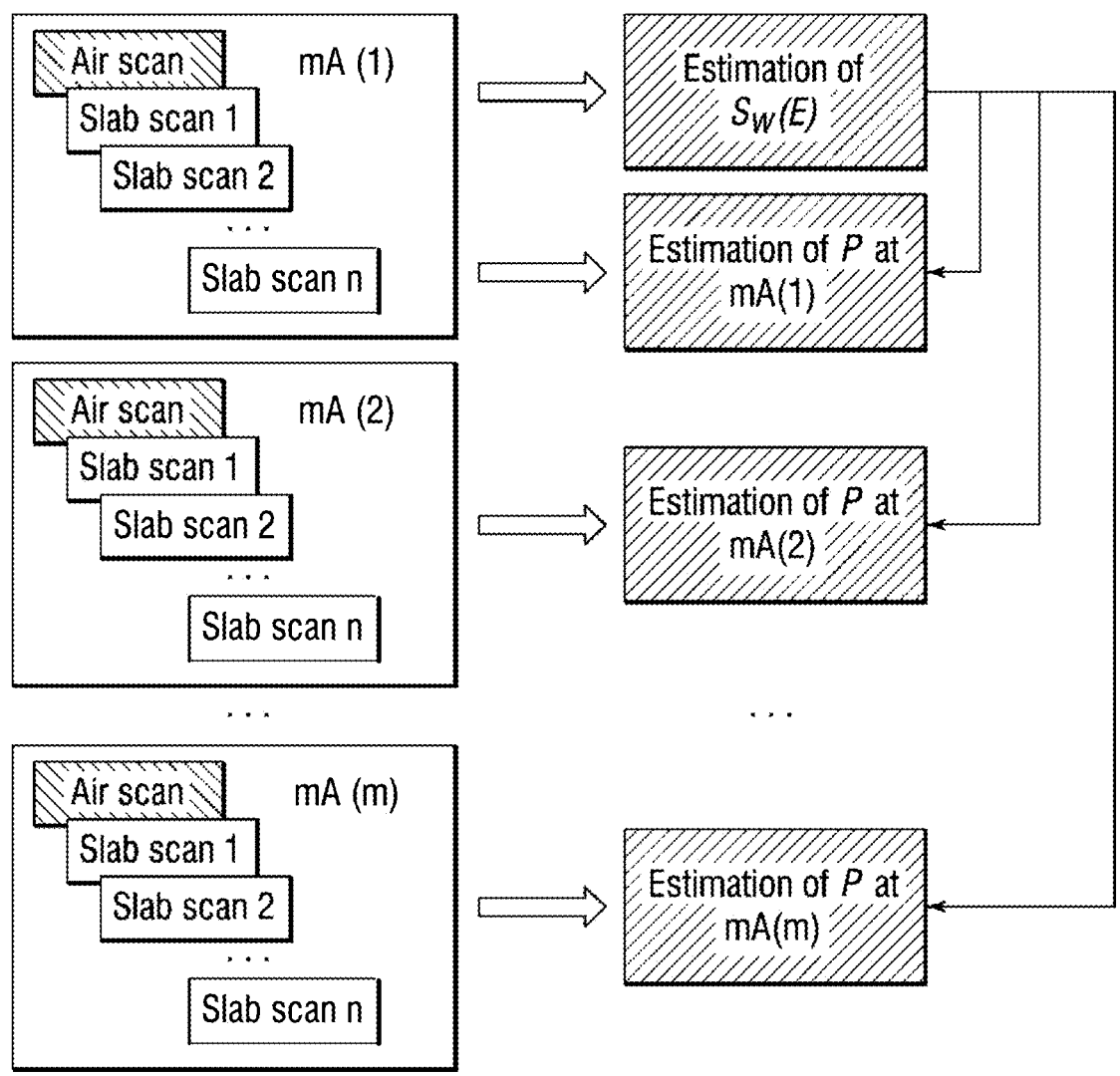
FIG. 4 shows a schematic of a calibration structure design, where the pileup correction tables $P_b$ are generated and used for each mA individually.
Figure 5:
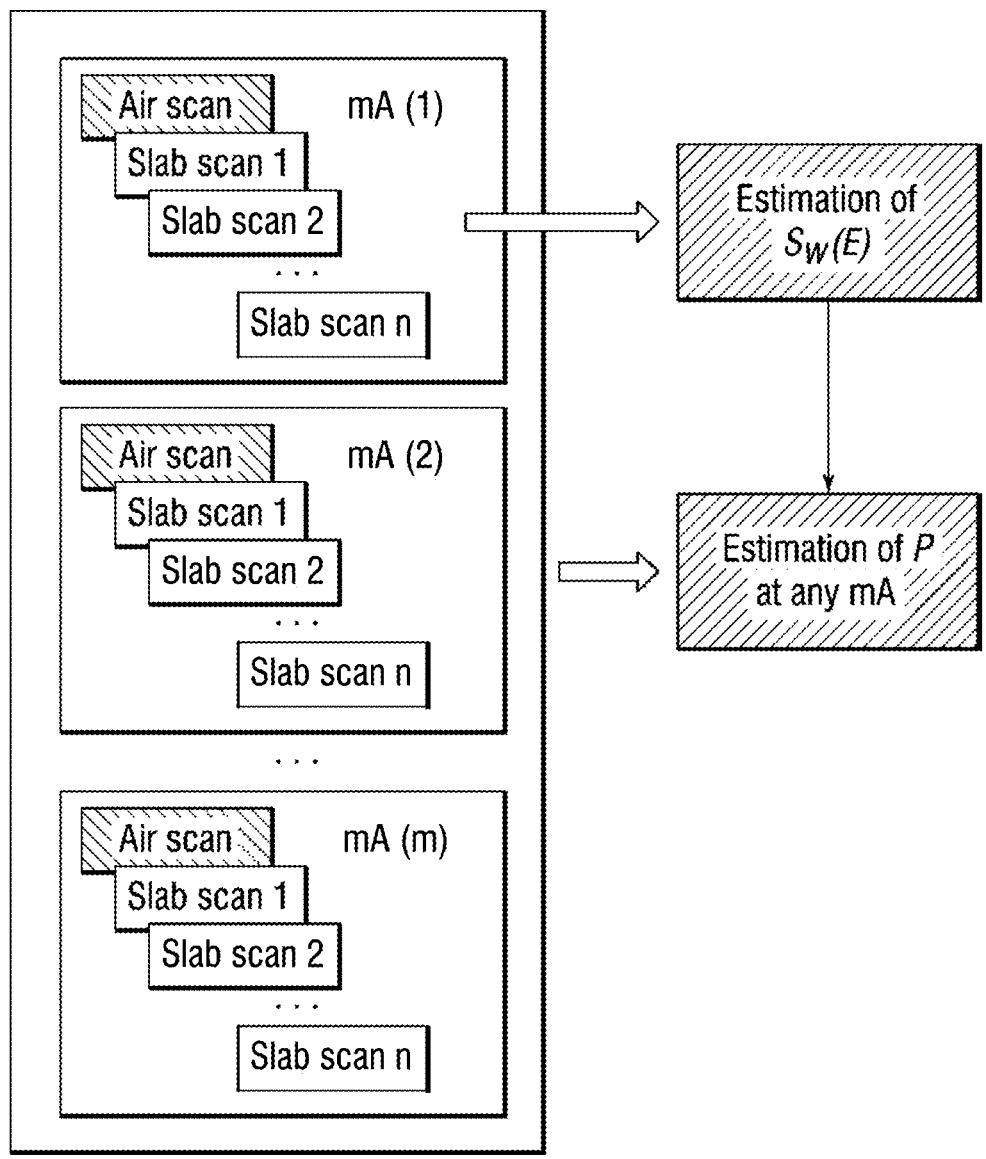
FIG. 5 shows a schematic of another calibration structure design, where a universal pileup correction table $P_b$ is generated for the entire mA range.

Two different calibration methods for the P term are illustrated in FIG. 4 and FIG. 5. The method of FIG. 4 calibrates P at a discrete current value mA and generates different correction tables for each mA setting, and the method of FIG. 5 calibrates P for the entire mA range (e.g., from low to high mA, from high to low mA, or with most frequently used values first) to generate a universal correction table for a continuous mA setting, which is a more challenging design that may need to use more parameters in P.

Beam Hardening Correction

The beam hardening correction (BHC) here is defined as the difference between eqs. (3) and eq. (4). The attenuation line integral $p_{mono}$ is defined as the logged counts for a monochromatic measurement, which is the input sinogram for FBP reconstruction:

$$p_{mono} = \left( \log \frac{N_{tot}}{N_0} \right)_{mono} = -\int \mu(E_0) dl \quad (11)$$

The logged count for a polychromatic measurement with the PCD response is:

$$p_{poly} = (\log N_{tot}/N_0)\text{poly} = \log(\int dES_w(E) * P(E, N_{tot}) * \exp(-\int \mu(E)dl)) \quad (12)$$

For BHC method 1, one can estimate the water equivalent path length $l_w$ by:

$$l_w = \frac{(\log N'_{tot}/N_0) poly}{\mu_w(E_0)} \quad (13)$$

Where $N'_{tot\_poly}$ is the detector response corrected total counts:

$$N'_{tot\_poly} = \frac{N_{tot}}{\int dES_w(E) * P(E, N_{tot})} \quad (14)$$

From eqs. (8) and (9), for detector i and view j, $$p_{mono}(i, j) = -\mu_w(E_0) l_w(i, j) \quad (15)$$

$$p_{poly}(i, j) = \log\left( \int dES_w(E) * P(E, N_{tot_{poly}}(i, j)) * \exp(-\mu_w(E) l_w(i, j)) \right) \quad (16)$$

Then, the beam hardening correction is calculated by:

$$BHC(i, j) = \quad (17)$$
$$\log\left( \int dES_w(E) * P(E, N_{tot\_poly}(i, j)) * \exp(-\mu_w(E) l_w(i, j)) - (-\mu_w(E_0) l_w(i, j)) \right)$$

and the corrected polychromatic line integral is obtained:

$$p_{corr}(i, j) = \left( \log \frac{N_{tot}}{N_0} \right) poly(i, j) - BHC(i, j) \quad (17a)$$

In one embodiment, the water path length $l_w$ can be calculated "on the fly" and the correction applied as in Eq. (17) and (17a).

In another embodiment, BHC(i,j) can be precalculated and resorted such that the input is the uncorrected count $N_{tot\_poly}$ and air flux $N_0$, and the output is the corrected count:

$$p_{corr}(i, j) = \left(\log\frac{N_{tot}}{N_0}\right)poly(i, j) - BHC'(N_{tot\_poly}(i, j), N_0) \quad (17b)$$

For BHC method 2, using a two-basis material based beam hardening correction, the basis material path lengths $l_1$, $l_2$ are estimated from the initial uncorrected image, for view i, channel j. The correction is calculated as below:

$$BHC(i, j) = \log(\int dES_w(E) * P(E, N_{tot\_poly}(i, j)) * \quad (18)$$
$$\exp(-\mu_1(E)l_1(i, j) - \mu_2(E)l_2(i, j)) -$$
$$(-\mu_1(E_0)l_1(i, j) - \mu_2(E_0)l_2(i, j))$$

$E_0$ is usually selected between 70-80 keV. Then the corrected projection sinogram $p_{corr}(i,j)$ is obtained for further reconstruction steps:

$$p_{corr}(i, j) = \left(\log\frac{N_{tot}}{N_0}\right)poly(i, j) - BHC(i, j) \quad (19)$$

Using the described methods, the beam hardening term is mostly based on calibration of a known material with minimum model dependence.

In one non-limiting embodiment of method 2, the basis material path lengths $l_1$ and $l_2$ can be estimated by segmenting the initial image into separated basis material images $IMG_1$ and $IMG_2$, and calculating $l_1$ and $l_2$ by forward projecting through $IMG_1$ and $IMG_2$.

In another non-limiting embodiment of method 2, $l_1$ and $l_2$ can be estimated from $IMG_1$ and $IMG_2$ using two-dimensional Fast Fourier Transform (FFT).

The disclosed counting detector response method is a novel calibration method specified for photon counting CT that combines the calibration and correction of X-ray spectrum, the PCD detector response, and the beam hardening effect. Compared to the conventional beam hardening calibration method, the disclosed method does not depend on the modelling of the X-ray tube spectrum and detail geometry of the beam pre-filtration, and the calculations are mostly based on calibration measurements for each individual pixel, and hence in practice can achieve better accuracy and better image quality.

In one non-limiting embodiment, measurements with multiple materials and known path lengths are used to calibrate the photon counting detector counting response of the forward model. The beam hardening corrections are then applied to the measured projection data sinogram and the corrected sinograms are reconstructed to the counting image at the selected single energy.

The count rate independent weighted total count response estimation employs EM method using low flux calibration data. The pulse pileup correction terms in the model are estimated at each high flux with the estimated weighted total count response function. The calibration tables are generated pixel by pixel, and can be scan protocols specific (kVp, mA, collimation, rotation speed etc.).

For the low flux weighted count response function estimation, an initial estimate with lower energy window than the default hardware setting can be used to accommodate any variation of the energy threshold in real detector performance.

An energy E and total count $N_{tot}$ based polynomial parameterization of the pileup model is designed to capture the detail detector counting performance based on the ideal non-paralyzable counting model.

A variation of the pileup model design is to include energy E, total count $N_{tot}$, and the individual energy bin count $N_b$ in the polynomial parameterization. The number of energy bins used can be between 2 to 6.

The dead time in the base non-paralyzable model can be set universally according to the default hardware setting (ASIC) or estimated pixel by pixel through a set of measurements from low to high mA. The measurements can be taken without scanning object (air scan) or with certain slab, e.g. 5-15 cm thick water, to cover the relevant flux range during a typical object scan.

The calibration scans at each kVp are conducted with individual bowtie/filter configuration and the tables are generated for each configuration used in object scans.

The calibration path length range is designed to cover the targeted scan object size/shape. The calibration path length samples or range can be the same for all the detector channels across the fan beam, or a sub-group of the samples can be used to target the path length range of the object scan for different detector channels located at different fan angle. The samples that are used for the calibration and the resulted tables can also be imaging task specific.

With the calibrated detector response, the beam hardening correction can be calculated on the fly with the initial estimated path length and the measured air flux $N_0$, object scan counts $N_{tot}$, or $N_{tot}$ and $N_b$.

The beam hardening correction can also be pre-calculated for each detector pixel at each estimated path length l and the count $N_{tot}$, (or with $N_b$), or for the measured air flux $N_0$, $N_{tot}$ (or with $N_b$).

In another non-limiting embodiment, an iterative beam hardening correction can also be applied using estimated basis material path lengths $l_1$, $l_2$. The basis material can be first segmented in the uncorrected images, and then the basis material path lengths for each view and each channel are estimated through a forward projection. This operation can go through multiple iterations until the beam hardening effect is minimized to acceptable level.

In addition to the total count image, the disclosed method can be applied to any energy bin measurement within the applicable energy threshold (e.g. 15 keV to max kVp of the tube). Each energy bin image can be reconstructed using the same approach with different beam hardening corrections.

Obviously, numerous modifications and variations of the present disclosure are possible in light of the above teachings. It is therefore to be understood that within the scope of the appended claims, the disclosure may be practiced otherwise than as specifically described herein.

The invention claimed is:

1. A method for calibrating a counting response of a photon counting detector (PCD) and for correcting for beam hardening, in a photon counting computed tomography (CT) system, the method comprising:
performing a plurality of low flux scans comprising an air scan and scans using a plurality of slabs of different materials, at an initial current intensity and at plural tube voltage settings of an X-ray tube, for each scan, to obtain counts for each energy bin;

estimating calibration parameters based on the counts, the calibration parameters being parameters for estimating the counting response of the PCD;

calculating beam hardening correction terms in object/patient scans based on the estimated calibration parameters; and generating a corrected counting image using the beam hardening correction terms.

2. The method according to claim 1, wherein the calculating beam hardening correction terms comprises:

estimating water equivalent path lengths from a sinogram based on projection measurement and calculating first beam hardening correction terms based on the estimated calibration parameters for each view and each detector channel.

3. The method according to claim 2, wherein the calculating beam hardening correction terms further comprises:

generating an uncorrected counting image, performing image segmentation of the uncorrected counting image into basis material images, performing forward projection on the basis material images to estimate path lengths, and calculating second beam hardening correction terms for each view and each detector channel.

4. The method according to claim 3, wherein the corrected counting image is generated based on the first beam hardening correction terms and second beam hardening correction terms.

5. The method according to claim 1, wherein the estimating the calibration parameters comprises:

estimating first parameters, which are dependent on energy, based on the counts;

estimating second parameters which are dependent on total counts of all energy bins, based on the first parameters; and repeating, using each of the plurality of slabs, the steps of estimating first and second parameters for different current intensities other than the initial current intensity and at the same tube voltage to obtain the second parameters, respectively, for the different current intensities, to generate tables of the estimated first parameters and second parameters.

6. The method according to claim 5, wherein an initial estimate of the first parameters is based on a lower energy window than a default hardware setting.

7. The method according to claim 6, wherein the initial estimate is based on of counts above $E_0$-x, where $E_0$ is a first energy threshold and 5 keV<x≤10 keV.

8. The method according to claim 5, wherein the first parameters depend on a bin response function.

9. The method according to claim 5, wherein the second parameters are related to pileup correction terms.

10. The method according to claim 5, wherein the second parameters are dependent on total counts of all energy bins and an individual energy bin count.

11. The method according to claim 1, further comprising repeating the calculating beam hardening correction terms in object/patient scans based on the estimated calibration parameters using an iterative beam hardening correction of an initial uncorrected sinogram from the object/patient scans until an image quality of the corrected counted image exceeds a predetermined threshold.

12. The method according to claim 11, further comprising assessing image quality of the corrected counting image and if the quality of the corrected counting image does not satisfy predefined standards, estimating basis material path lengths from a reconstructed image for the beam hardening correction.

13. The method according to claim 1, wherein the calibration is performed pixel by pixel.

14. The method according to claim 1, wherein calibration scans at the plural tube voltage settings are conducted with respective bowtie/filter configurations and calibration tables are generated for each configuration used in the object scans.

15. The method according to claim 1, wherein the estimating calibration parameters based on the counts comprises:

estimating first parameters, which are dependent on energy, based on the counts;

repeating, using each of the plurality of slabs, the step of performing a plurality of low flux scans for different current intensities other than the initial current intensity and at the same tube voltage, to obtain a universal table of estimated second parameters which are dependent to total counts of all energy bins based on the first parameters, in the entire current intensity range.

16. The method according to claim 15, wherein the step of calculating beam hardening correction terms comprises:

estimating water equivalent path lengths from a sinogram based on projection measurement and calculating first beam hardening correction terms based on the estimated calibration parameters for each view and each detector channel.

17. The method according to claim 16, wherein the step of calculating beam hardening correction terms comprises:

generating an uncorrected counting image, performing image segmentation of the uncorrected counting image into basis material images, performing forward projection on the basis material images to estimate path lengths, and calculating second beam hardening correction terms for each view and each detector channel.

18. The method according to claim 17, wherein the corrected counting image is generated based on the first beam hardening correction terms and the second beam hardening correction terms.

* * * * *